United States Patent [19]

Fattaleh

[11] 4,432,729

[45] Feb. 21, 1984

[54] PERSONAL HEALTH CARE DEVICE

[76] Inventor: John B. Fattaleh, 4937 N. 43rd St., Phoenix, Ariz. 85018

[21] Appl. No.: 370,878

[22] Filed: Apr. 23, 1982

[51] Int. Cl.³ ............................ A61C 1/07; A61C 3/03
[52] U.S. Cl. ..................................... 433/118; 15/22 R
[58] Field of Search ....................... 433/118, 122, 125;
128/62 A; 15/28, 22 R

[56] References Cited

U.S. PATENT DOCUMENTS

| | | | |
|---|---|---|---|
| 149,442 | 4/1874 | Clancey | 433/122 |
| 1,335,825 | 4/1920 | Ellerbeck. | |
| 2,406,113 | 8/1946 | Silver | 32/26 |
| 3,195,537 | 7/1965 | Blasi | 128/62 A |
| 3,555,685 | 11/1968 | Loge | 32/57 |
| 3,578,745 | 5/1968 | Garnier | 32/57 |
| 3,802,420 | 4/1974 | Moffett et al. | 128/62 A |
| 3,921,298 | 11/1975 | Fattaleh | 32/58 |
| 4,289,849 | 9/1981 | Lustig | 433/123 |

Primary Examiner—Robert Peshock
Attorney, Agent, or Firm—Cates & Roediger

[57] ABSTRACT

A hand-held personal health care device for the polishing of teeth wherein the appliance containing the cleaning agent is driven in an oscillatory manner.

23 Claims, 5 Drawing Figures

U.S. Patent  Feb. 21, 1984  4,432,729
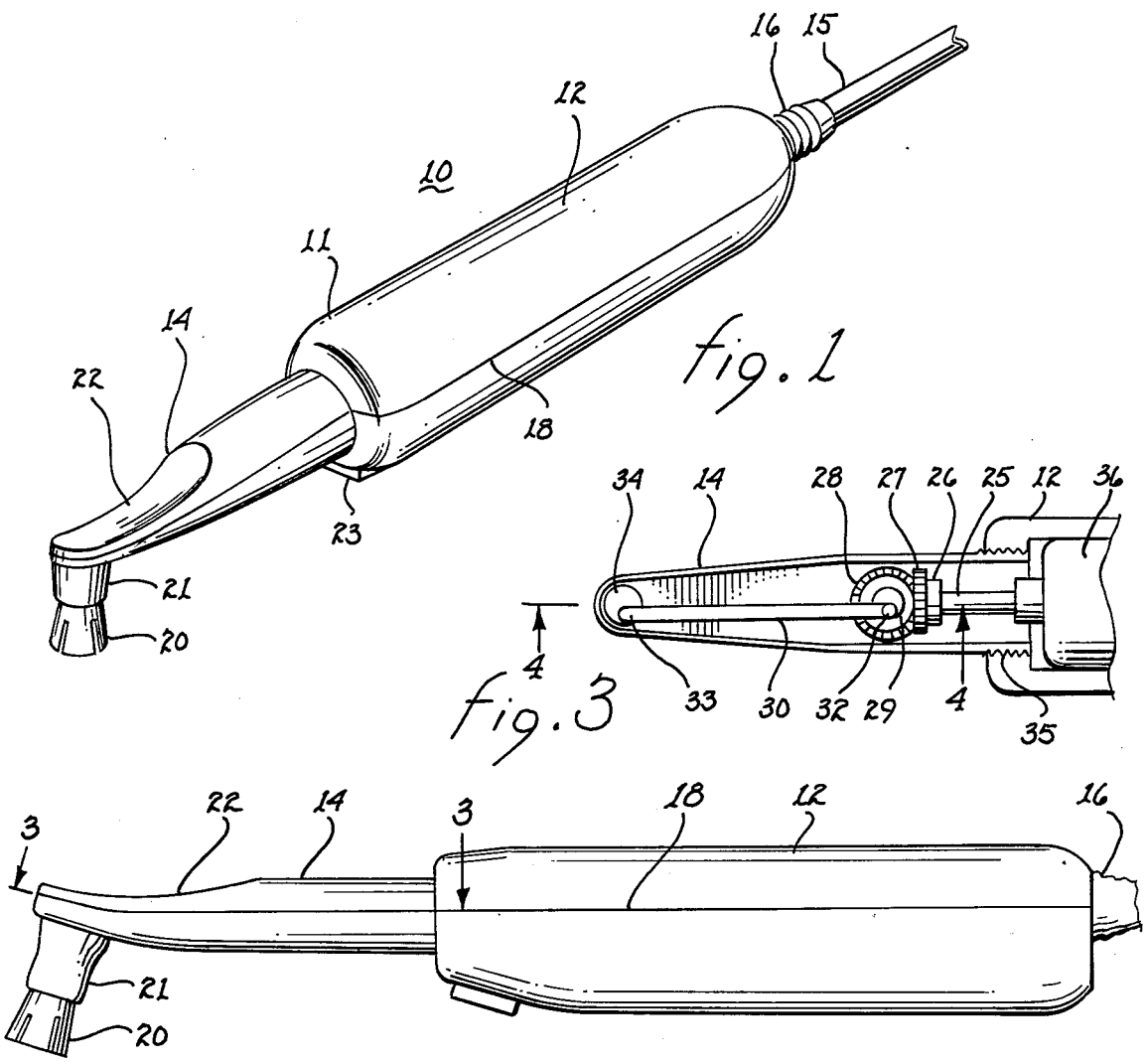
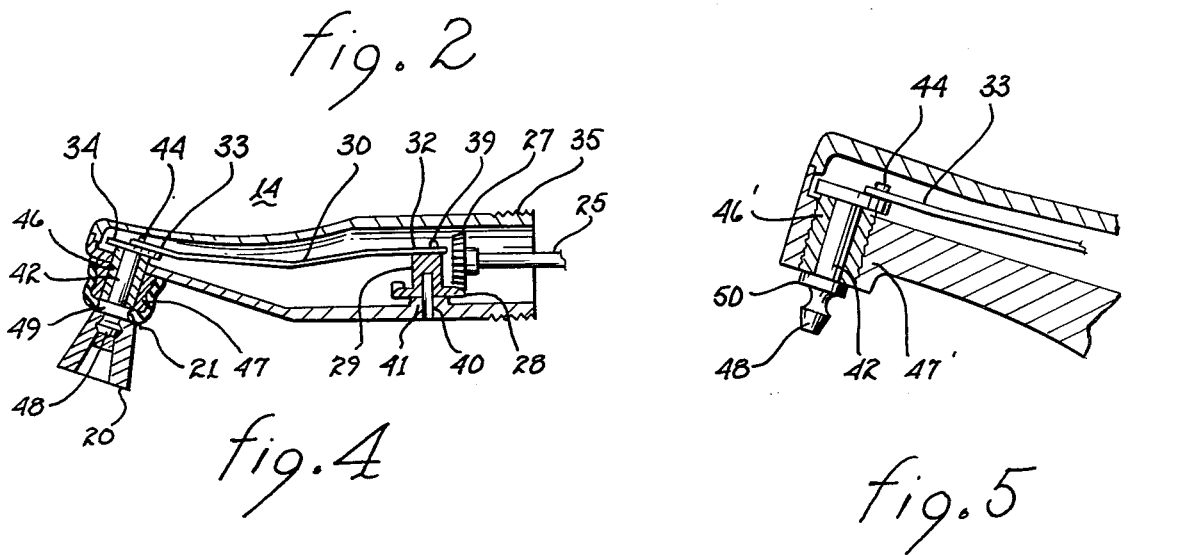

PERSONAL HEALTH CARE DEVICE

BACKGROUND OF THE INVENTION

The benefits to health derived from the continual periodic cleansing of teeth by an individual has been clearly demonstrated over the years. In order to obtain these benefits, the selection of an appropriate type of personal health care device to provide the desired cleansing and polishing effects has been found most important.

The combined utilization of bacteria disturbing vehicles for use at and below the gum line, such as dental tape and floss, along with a thorough cleansing and polishing of the exposed surfaces of the teeth are now generally accepted by the professionals in the dental field as providing the best practical care. While the conventional toothbrush is the most common personal device employed, the dental professional utilizes a flexible rotating cleansing-polishing appliance which contains the cleansing agent therein. Numerous attempts have been made to provide a similar hand-held device for individual usage at locations remote from the specialized equipment and drive mechanisms which are common to the professional office.

Size and shape of the device are primary considerations since the operative end must be capable of manipulation throughout the mouth in order to contact the exposed surfaces of the teeth. In addition, dental care devices require that the portion containing the particular appliance for the task at hand be angled with respect to the axis of the main body of the device in order to insure that the appliance effectively contacts the multiple faces of the teeth.

At present, the need for slim line, hand-held personal health care devices has generated a family of products capable of providing a cleansing and polishing effect and which is intentionally made small for insertion into the oral cavity and angled from the body of the device to facilitate hand manipulation by the individual unskilled user. One such device is disclosed in my prior U.S Pat. No. 3,921,298 wherein continuous rotational motion via flexible drive means of an appliance provides polishing and cleansing functions.

One common problem in the design of these small devices with tapered angled operative ends is the accommodation of a motion translating mechanism in the small cross sectional area available. The hand-held device typically utilizes an electric motor connected to either an internal or external power supply with a rotating shaft extending axially within the housing. In applications wherein continuous rotational movement of the appliance is the desired end, it is known to provide a flexible belt and pulley drive mechanism within the narrow confines of the angular operating end. In the operation of this type of device for home usage, the operating conditions are not controlled by professionally-trained staff and the varying pressures applied by the user often lead to undue heat generation at the tooth surface, internal belt slippage and a frequent need to replace the belting. While the flexible belt drive is found satisfactory under many conditions it provides continual rotational movement of the appliance. While this type of movement is acceptable under controlled conditions, an individual operator failing to turn the device off while it remains within the oral cavity causes residual matter on the appliance to fly about the area.

Accordingly, the present invention is directed to a personal health care device for use by individuals wherein the small cross-sectional area of the operating end includes an oscillatory drive mechanism. In addition, the appliance is located proximate to the small end region of an angled operating end to facilitate manipulation by the user. Further, the oscillating drive mechanism provides a positive direct linking between the internal drive and driven means to substantially eliminate internal slippage and reduce the need for the replacement of parts therein.

SUMMARY OF THE INVENTION

The present invention relates to a personal health care device for use by individuals without the direct supervision or control of professional staff. The device is especially well-suited for use in polishing and cleaning the exposed surfaces of teeth.

The device includes a containment means for housing a drive mechanism and has an operative end of small cross-sectional area and a hand-grippable body portion. The operative end is constructed so that at least a portion thereof is angled with respect to the axis of the body for enhancing the efficacy of the device.

A power drive means is mounted within the containment means and either an external electrical connection can be provided or rechargeable battery operation can be utilized. The nature of the power supply can be selected by the type of usage expected. The power drive means includes an output shaft which rotates upon actuation of suitable control means and extends substantially axially along the body portion of the containment means. A drive means is mounted for rotation about a first axis within the operating end and is operatively coupled to the output shaft.

Also, the operative end includes driven means mounted therein for rotation about a second axis. The driven means has an engaging means affixed thereto which extends outwardly of the operative end for removably receiving an appliance thereon. A non-planar connection means is coupled to both the drive and the driven means to permit incorporation within the angled operative end. In addition, the connection means is coupled to impart oscillatory motion to the driven means. This is accomplished by coupling one end of the connection means to the drive means a first distance from the first axis while coupling the opposing end to the driven means a second distance from the second axis. The first distance is less than the second distance so that a 360 degree rotation of the drive means in response to the drive shaft results in an oscillatory movement of the driven means about the second axis.

The engaging means affixed to the driven means is therefore provided with an oscillatory movement. The engaging means which extends outwardly of the operative end via a suitable bushing is provided with an expanded diameter end for removably receiving an appliance, typically a conventional cleansing-polishing cup with a ribbed external cavity for receiving paste material to be applied to the surfaces of the teeth.

Further features and advantages of the invention will become more readily apparent from the following detailed description of specific embodiments of the invention when taken in conjunction with the accompanying drawings.

BRIEF DESCRIPTION OF THE DRAWINGS

FIG. 1 is a view in perspective of one embodiment of the invention.

FIG. 2 is a side view of the embodiment of FIG. 1.

FIG. 3 is a top view in section taken along line 3—3 of FIG. 2.

FIG. 4 is a side view in section taken along line 4—4 of FIG. 3.

FIG. 5 is a side view in section similar to FIG. 4 of another embodiment of the invention.

DESCRIPTION OF THE PREFERRED EMBODIMENT

Referring now to the embodiment of FIGS. 1 and 2, a personal health care device 10 is shown including containment means 11 having a hand-grippable body portion 12 with external switch button 23 and an operating end 14 of reduced cross-sectional area. The opposing end of containment means 11 is provided with external electrical connection 15 having a flexible waterproof reinforcing section 16 provided adjacent the containment means. However, the external a-c connection may be replaced by internal battery means as the power supply with conventional recharging receptacles provided for the external connection. The containment means is formed in upper and lower sections as indicated by parting line 18 in order to permit assembly and testing prior to forming the sealed unit. This feature provides distinct manufacturing advantages.

At the end of operating end 14, a region 22 of substantially reduced cross-sectional area is angularly displaced in an upward direction from the longitudinal axis of the body portion 12. This orientation of the portion of the device placed within the oral cavity of the user facilitates the manipulation of the device by the user to permit the contact of appliance 20 with the variously oriented surfaces of the teeth. The combination of small cross-sectional area and angular displacement in the operative end have heretofore tended to limit the types of drive mechanisms available for use therein while favoring the use of flexible belt drives and their 360 degree rotational drive of the tip-mounted accessory 20. The present invention utilizes a novel drive assembly which is readily accommodated in this type of containment means and provides a different drive motion for the accessory 20.

The accessory 20 is generally a flexible cup containing internal ribs or vanes within the cup. In operation, a cleansing-polishing agent is added to the cup and the cup is placed in contact with the surface of the teeth. Heretofore, the 360 degree rotation of such accessories has placed the burden on the user to actuate the device after it is within the oral cavity to prevent the agent from being sprayed about. This result has tended to reduce consumer acceptance of devices of this type. The present invention providing an oscillatory motion of the accessory 20 does not generate this undesirable result nor does it create the heat of a continually rotating head which often leads to user discomfort.

The manner of affixation of the accessory 20 to the engaging means is not apparent from viewing FIGS. 1 and 2 since, in operation, a flexible sleeve or boot 21 is provided between the accessory and region 22 of the operative end. The sleeve frictionally engages the extended portion of the operative end as well as the extension of the shaft of the oscillating engaging means which extends from the device, as shown in detail in FIG. 4. The sleeve assists in establishing a water-tight device and can be utilized because the output motion of the device is oscillatory rather than complete rotation. The provision of this barrier is important not only from a safety standpoint but also to the operating lifetime of the device since cleansing-polishing agents are abrasive by their nature and their migration into the workings of the drive mechanism has been found to result in damage to the mechanism.

The drive mechanism is shown in detail in the partial sectional view of FIG. 3 wherein the upper section of containment means 11 is removed to provide a view of the interior of the operating end 14. The power drive module 36, typically a d-c electrical motor, has an output shaft 25 which axially extends into the operating end and is provided with support plate 26 having circular gear 27 affixed thereto. The actuation of the power drive module results in the rotation of gear 27.

The power drive module 36 is provided as shown with internal threads for receiving the external threads 35 of the operating end. The ability to use the power drive module with other operating ends for multiple user capability is present. In other embodiments of the invention, the operating end and the power drive module can be made integral if desired. In addition it should be noted that the extension of the drive shaft 25 into the operating end is preferred, however the power drive module can incorporate the entire output shaft and circular gear 27 if desired.

As shown, the drive means in the operative end includes the gear 28 centrally mounted on a substantially vertical axis and having upstanding gear teeth which mesh with the teeth of circular gear 27. Consequently, the rotational drive from the power module is translated through an angle of ninety degrees. Horizontal gear 28 is provided with a raised central portion 29 upon which one end 32 of the connecting link 30 is movably mounted for rotation in a horizontal plane. The end 32 is mounted on the raised portion 29 at a point spaced from the vertical rotational axis on gear 28. As gear 28 is driven through a complete rotation, the end of the connecting link moves about a circular path having a radius equal to the distance between the mounting and the axis of rotation of gear 28.

Driven means 34 is shown as a disc and is mounted for rotation about a central off-vertical axis, shown more clearly in FIG. 4. The opposing end 33 of the connecting link 30 is rotatably attached at the upper surface of driven means 34 at a distance from the axis of rotation thereof. This distance is greater than the spacing of end 32 from the axis of rotation of gear 28 so that one revolution of gear 28 results in end 33 and driven means 34 transversing an arc of less than 180 degrees. In the preferred embodiment, the ratio of the distances for the ends 32 and 33 of link 30 is made such that the driven disc 34 traverses and arc of about 120 degrees. One revolution of gear 28 provides two traverses of the arcuate path or one oscillatory cycle for the disc 34.

In FIG. 4, the gear 27 on the output shaft is shown meshing with gear 28 mounted for rotation about a vertical axis defined by shaft 40. The shaft 40 is normally press fit into a mounting sleeve 41 bonded to or molded in the underside of the operating end 14. The gear 28 contains an integral raised central portion at the top of which is rotatably pinned the end 32 of connecting link 30. Pin 39 is shown offset from the vertical axis of gear 28 as defined by shaft 40.

The opposing end 33 of connecting link 30 is movably coupled to the top surface of driven disc 34 by pin 44. The coupling pin is spaced from the axis of movement of the disc as defined by shaft 42 by a distance greater than the offset spacing of end 32. In order to accommodate the combination of drive gear, driven disc and connecting link within the angled cross-sectional area of the operating end 14, the rigid connecting link is non-planar with the opposing ends essentially perpendicular to the axes of rotation of the drive gear and driven disc. The axes are non-parallel due to the angular displacement of region 22. The portion of the connecting link between the opposing ends is shown comprised of two non-planar segments oriented to provide the coupling for transmittal of the force. Other configurations of the central portion of the link may be utilized if desired.

The shaft 42 of the driven disc 34 is journalled in a split sleeve bearing 46 which is affixed to the perimetrical surface of a hole formed in the underside of the operating end. The disc is preferably made integral with the engaging means for receiving the appliance 20 and is shown affixed to the end of shaft 42 which terminates at its outer end in expanded diameter portion 48. The flexible accessory is urged onto the engaging means by forcing its receiving end over portion 48.

Also, shaft 42 has an intermediate section 49 of large diameter serving as a thrust plate with a concave peripheral surface. Adjacent section 49 is the bearing 46 for shaft 42 so that axial movement of the driven disc and the engaging means is limited. A housing 47 for bearing 46 is placed over the engaging means and moved upwardly to be fastened to both the outer surfaces of the operating end and the bearing 46. The housing 47 is shown having a centrally located concave peripheral portion.

The cylindrical sleeve 21 formed of a water impermeable material serves as a water-tight boot that prevents the entrance of the cleansing-polishing agent into the operating end of the invention thereby substantially increasing the service life of the device. The boot can be independently replaced by removing the appliance 20 and sliding the new sleeve over the concave portion 49 of the engaging means onto the housing 47 and its concave portions. The nature of the oscillatory motion of the shaft 42 permits the use of a tight flexible sleeve to cover bearing joints as contrasted with the exposed joints found in fully rotational equipment.

The use of a longitudinally divided containment means permits the installation and testing of the compartments of the invention prior to sealing. The mounting of the power drive means and the associated switch in the containment means can be selected by the manufacturer in accordance with the type of drive motor and power source favored. Reference to external connections in hand held appliances may be found in my U.S. Pat. No. 3,921,298 issued Nov. 25, 1975.

A second embodiment of the invention is shown in FIG. 5 with like parts having the same reference numerals. This embodiment utilizes a threaded split bearing 46' which is placed about shaft 42 and threaded into receiving housing 47' molded as a portion of the operating end. The insertion of the piece part takes place from the top prior to the affixation of the top portion of the containment means. A thrust plate 50 is located on the shaft 42 to limit axial movement. The shaft terminates in an expanded diameter portion 48 which receives the appliance to be driven. The connection of the driven disc to the drive gear is the same for each embodiment. If desired, a flexible boot can be provided by the use of a right-angle sheath extending over the end and contacting the sides of the thrust plate 50.

While the above description has referred to specific embodiments of the invention, it is recognized that many variations and modifications may be made therein without departing from the scope of the invention.

I claim:

1. A personal health care device comprising:
   (a) containment means for housing a drive mechanism therein and having an operative end and a body portion;
   (b) power drive means mounted in said containment means and having an output shaft extending therefrom, the actuation of said power drive means providing rotation of said output shaft;
   (c) drive means mounted for rotation about a first axis at an angle to the axis of said output shaft and operatively coupled thereto;
   (d) driven means mounted in said operative end for rotation about a second axis at an angle to the axis of said output shaft;
   (e) an elongated rigid link coupled to said drive means a first distance from said first axis and coupled to said driven means a second distance from said second axis, said first distance being less than said second distance whereby rotation of said drive means imparts an oscillatory motion to the rotation of said driven means;
   (f) engaging means affixed to said driven means and extending outwardly of said operative end for receiving an appliance thereon.

2. The device of claim 1 wherein at least a portion of said operative end is angled from the body portion of said containment means.

3. The device of claim 2 wherein said engaging means extends outwardly of the angled portion of said operative end.

4. The device of claim 3 wherein said engaging means comprises an expanded diameter end for removably receiving an appliance thereon.

5. The device of claim 4 further comprising sealing means coupled between said engaging means and the operative end of said containment means.

6. The device of claim 5 wherein said sealing means is flexible sleeve frictionally engaging the operative end of said containment means and said engaging means.

7. The device of claim 6 wherein said elongated rigid link is non-planar and comprises first and second end segments substantially parallel with the drive means and the driven means respectively and a connecting segment therebetween.

8. The device of claim 3 further comprising a bearing means affixed to the angled portion of said operative end for rotatably receiving a portion of said engaging means therein.

9. The device of claim 8 wherein said bearing means comprises a section of reduced diameter and said engaging means has a section of reduced diameter, said sealing means being frictionally coupled to said sections of reduced diameter and extending therebetween.

10. The device of claim 9 wherein said elongated rigid link is non-planar and comprises first and second end segments substantially parallel to the drive means and the driven means respectively and a connecting segment therebetween.

11. The device of claim 10 wherein said first and second axes are non-parallel with respect to each other.

12. The device of claim 11 wherein the operative end of said containment means is removably affixed to the body portion thereof, said power drive means being mounted in said body portion and having the output shaft extending therefrom.

13. A personal health care attachment having an operative end and a securing end for use with a power drive module having an externally accessible power drive means, said attachment comprising:
   (a) means for removably affixing the securing end of said attachment to the power drive module;
   (b) drive means mounted for rotation about a first axis at an angle to the axis of said power drive means and operatively coupled thereto;
   (c) driven means mounted in the operative end of said attachment for rotation about a second axis at an angle to the axis of said power drive means;
   (d) an elongated rigid link coupled to said drive means a first distance from said first axis and coupled to said driven means a second distance from said second axis, said first distance being less than said second distance whereby rotation of said drive means imparts an oscillatory motion to the rotation of said driven means;
   (e) engaging means affixed to said driven means and extending outwardly of the operative end of said attachment for receiving an appliance thereon.

14. The attachment of claim 13 wherein at least a portion of said operative end is angled from the body portion of said attachment.

15. The attachment of claim 14 wherein said engaging means extends outwardly of the angled portion of said operative end.

16. The attachment of claim 15 wherein said engaging means comprises an expanded diameter end for removably receiving an appliance thereon.

17. The attachment of claim 16 further comprising sealing means coupled between said engaging means and the operative end of said attachment.

18. The attachment of claim 17 wherein said sealing means is a flexible sleeve frictionally engaging the operative end of said attachment and said engaging means.

19. The attachment of claim 18 wherein said elongated rigid link is non-planar and comprises first and second end segments substantially parallel with the drive means and the driven means respectively and a connecting segment therebetween.

20. The attachment of claim 15 further comprising a bearing means affixed to the angled portion of said operative end for rotatably receiving a portion of said engaging means therein.

21. The attachment of claim 20 wherein said bearing means comprises a section of reduced diameter and said engaging means has a section of reduced diameter, said sealing means being frictionally coupled to said sections of reduced diameter and extending therebetween.

22. The attachment of claim 21 wherein the elongated rigid link comprises first and second end segments substantially parallel to the drive means and the driven means respectively and a connecting segment therebetween.

23. The attachment of claim 22 wherein said first and second axes are non-parallel with respect to each other.

* * * * *